United States Patent [19]

Horwell et al.

[11] Patent Number: 4,663,343

[45] Date of Patent: * May 5, 1987

[54] SUBSTITUTED NAPHTHALENYLOXY-1,2-DIAMINOCYCLOHEXYL AMIDE COMPOUNDS

[75] Inventors: David C. Horwell, Foxton, England; David Schofield, Cherry Hinton, United Kingdom

[73] Assignee: Warner-Lambert Company, Morris Plains, N.J.

[ * ] Notice: The portion of the term of this patent subsequent to Jul. 1, 2003 has been disclaimed.

[21] Appl. No.: 756,634

[22] Filed: Jul. 19, 1985

[51] Int. Cl.$^4$ .................... C07D 207/06; A61K 31/40
[52] U.S. Cl. .................................... 514/429; 546/234; 548/517; 548/527; 548/578; 564/162; 564/172
[58] Field of Search ......................... 548/578; 514/429

[56] References Cited

U.S. PATENT DOCUMENTS

| | | | |
|---|---|---|---|
| 4,098,904 | 7/1978 | Szmuszkovicz | 548/578 |
| 4,145,435 | 3/1979 | Szmuszkovicz | 514/429 |
| 4,598,087 | 7/1986 | Horwell | 548/578 X |

*Primary Examiner*—Joseph Paul Brust
*Attorney, Agent, or Firm*—Jerry F. Janssen

[57] ABSTRACT

Substituted naphthalenyloxy- or naphthalenylthiooxyamides of trans-1,2-diaminocyclohexanes possess selective kappa opioid receptor site binding activity and are thus useful as analgesic or diuretic agents. Methods of preparing the compounds, pharmaceutical compositions, and a method for their use as analgesic agents are also disclosed.

14 Claims, No Drawings

SUBSTITUTED NAPHTHALENYLOXY-1,2-DIAMINOCYCLOHEXYL AMIDE COMPOUNDS

BACKGROUND OF THE INVENTION

The search for strong analgesics which also possess minimal potential for dependency has been among the highest priority efforts in pharmacological research. These research efforts have, to a great extent, involved chemical modifications of the opiate structure and the discovery of chemically novel compounds which possess morphine-like activity.

The discovery of endogenous polypeptide opioids has led workers in the field to consider that these peptides, possessing less rigid structures, might interact with opioid receptors other than those to which the classical rigid structure opiates, such as morphine, bind.

The concept of multiple opioid receptors has been supported by studies with nalorphine and a series of benzomorphans which display unusual pharmacological properties dissimilar from morphine, yet blocked by selective opioid antagonists. [See for example, W. R. Martin et al., *J. Pharmacol. Exp. Ther.*, 197: 517–532 (1976)].

The existence of multiple types of opioid receptors is of importance because of the possibility of separating desirable analgesic and psychotherapeutic effects of a drug compound from the undesirable abuse potential or habituating effects.

U.S. Pat. No. 4,145,435 describes certain 2-aminocycloaliphatic amide compounds as analgesics. In particular, trans-3,4-dichloro-N-methyl-N-[2-(1-pyrrolidinyl)cyclohexyl]benzacetamide has been reported to possess selective kappa opioid receptor agonist activity, and therefore to possess analgesic activity without attendant dependence liability. [See P. V. Vanvoigtlander et al., *J. Pharmacol. Exp. Ther.*, 224: 7–12 (1983)].

Recently the diuretic effect of various opioid agonists and antagonists has been studied, and it has been shown that kappa agonists tend to increase urination, while mu agonists decrease urination. [See J. D. Leander, *J. Pharmacol. Exp. Ther.*, 227: 35–41 (1983)]. These findings indicate that selective opioid agonists and antagonists also possess potential as diuretics.

SUMMARY OF THE INVENTION

The present invention relates to substituted trans-1,2-diaminocyclohexyl acetamide compounds useful as analgesics or diuretic agents. The invention is also concerned with a method of preparing such compounds, pharmaceutical compositions including such compounds, and with a method of alleviating pain in a mammal by administering to a mammal in need of such treatment an analgesically effective amount of a compound in accordance with the present invention, together with a suitable pharmaceutically acceptable carrier.

In its broadest aspect, the present invention provides compounds having structural formula 1

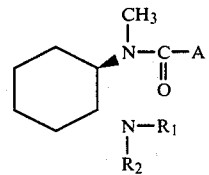

wherein $R_1$ is methyl and $R_2$ is hydrogen, alkyl of from one to six carbon atoms,

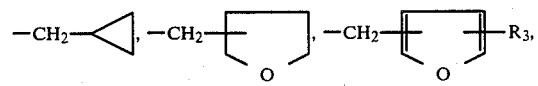

$-CH_2C=CCR_3R_4$, $-CH_2C\equiv CH$, 2- or 3-thienyl, or

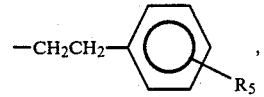

where $R_3$ and $R_4$ are independently hydrogen or methyl, and $R_5$ is hydrogen, fluorine, chlorine, bromine, alkyl of from one to four carbon atoms, alkoxy of from one to four carbon atoms; or where $R_1$ and $R_2$ taken together with the nitrogen atom to which they are attached form a ring denoted by

where m is an integer of from three to eight; and where A is

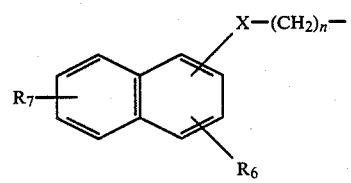

where n is an integer of from one to six; X is oxygen or sulfur; and $R_6$ and $R_7$ are independently fluorine, chlorine, bromine, nitro, acetoxy, alkyl of from one to four carbon atoms, or alkoxy of from one to four carbon atoms.

Also contemplated as falling within this aspect of the invention are the $N^1$-oxides of compounds having structural formula 1 above. The meaning of the term "$N^1$-oxides" is made clear by reference to structural formula 1a below in which the nitrogen atoms have been numbered. The alkyl-substituted nitrogen has been numbered "2" and the amido-nitrogen has been numbered "1".

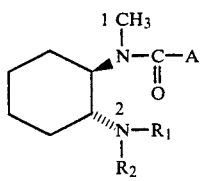

Oxidation of compounds of structural formula 1 above with, for example, m-chloroperbenzoic acid or other similar suitable oxidizing agents, converts the more basic alkyl-substituted nitrogen atom (1) to the corresponding N-oxide.

In accordance with a second aspect of the present invention, a method of preparing compounds having structural formula I comprises the steps of reacting a trans-cyclohexyldiamine compound of structural formula 2

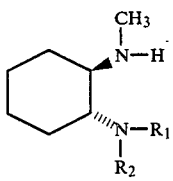

with a substituted carboxylic acid of structural formula 3 in the presence of a coupling reagent such as dicyclohexylcarbodiimide or with a reactive derivative of an acid of formula 3 such as the corresponding acid chloride or acyl imidazole.

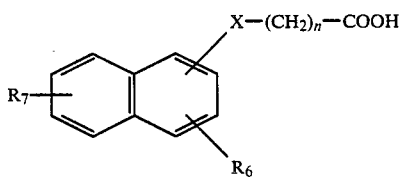

In accordance with another aspect of the present invention, pharmaceutical compositions useful for alleviating pain in a mammal comprise an analgesically effective amount of a compound having structural formula 1 above in combination with a pharmaceutically acceptable carrier.

In a further aspect, the present invention provides a method of alleviating pain in a mammal comprising administering to a mammal in need of such treatment an analgesically effective amount of a compound having structural formula 1 above in combination with a pharmaceutically acceptable carrier.

DETAILED DESCRIPTION

Compounds of the present invention comprise a class of derivatives of trans-1,2-diaminocyclohexane in which one nitrogen is an amine nitrogen substituted with methyl and a second substituent selected from the group $R_2$ as defined above or, preferably is a tertiary amine nitrogen atom which is part of a dimethylamino group or a nitrogen-heterocyclic pyrrolidinyl, piperidinyl, or hexahydro-1H-azepinyl ring. The other nitrogen atom of the 1,2-diaminocyclohexane moiety is an N-methyl amide nitrogen further substituted with the group A as defined above.

Compounds of the present invention contain one or more asymmetric carbon atoms and therefore exist as enantiomers or diastereomers. The present invention contemplates all possible geometric and stereoisomeric forms of the compounds of structural formula 1 above. Individual stereoisomers are obtained, if desired, from mixtures by known methods of resolution.

In a preferred embodiment, the present invention provides compounds of structural formula 1 above where X is oxygen and $R_1$ and $R_2$ combine to form a pyrrolidinyl ring.

The following are examples of compounds falling within the scope of the present invention:

trans-N-Methyl-2-(1-naphthalenyloxy)-N-[2-(1-pyrrolidinyl)cyclohexyl]acetamide;

trans-N-Methyl-2-(2-naphthalenyloxy)-N-[2-(1-pyrrolidinyl)cyclohexyl]acetamide;

trans-N-Methyl-2-[(2-methyl-1-naphthalenyl)oxy]-N-[2-(1-pyrrolidinyl)cyclohexyl]acetamide;

trans-2-[(2-Chloro-1-naphthalenyl)oxy]-N-methyl-N-[2-(1-pyrrolidinyl)cyclohexyl]acetamide;

trans-2-[(4-Chloro-1-naphthalenyl)oxy]-N-methyl-N-[2-(1-pyrrolidinyl)cyclohexyl]acetamide;

trans-2-[(2,4-Dichloro-1-naphthalenyl)oxy]-N-methyl-N-[2-(1-pyrrolidinyl)cyclohexyl]acetamide;

trans-2-[(2-Acetoxy-1-naphthalenyl)oxy]-N-methyl-N-[2-(1-pyrrolidinyl)cyclohexyl]acetamide;

trans-2-[(4-Methoxy-1-naphthalenyl)oxy]-N-methyl-N-[2-(1-pyrrolidinyl)cyclohexyl]acetamide;

trans-N-Methyl-2-(2-nitro-1-naphthalenyloxy)-N-[2-(1-pyrrolidinyl)cyclohexyl]acetamide;

trans-N-[2-(Dimethylamino)cyclohexyl]-N-methyl-2-(1-naphthalenyloxy)acetamide;

trans-N-[2-(Dimethylamino)cyclohexyl]-N-methyl-2-(2-naphthalenyloxy)acetamide;

trans-N-[2-(Dimethylamino)cyclohexyl]-N-methyl-2-[(2-methyl-1-naphthalenyl)oxy]-acetamide;

trans-2-[(2-Chloro-1-naphthalenyl)oxy-N]-methyl-N-[2-(dimethylamino)cyclohexyl]acetamide;

trans-2-[(4-Chloro-1-naphthalenyl)oxy]-N-methyl-N-[2-(dimethylamino)cyclohexyl]acetamide;

trans-2-[(2,4-Dichloro-1-naphthalenyl)oxy]-N-methyl-N-[2-(dimethylamino)cyclohexyl]acetamide;

trans-2-[(2-Acetoxy-1-naphthalenyl)oxy]-N-methyl-N-[2-(dimethylamino)cyclohexyl]acetamide;

trans-2-[(4-Methoxy-1-naphthalenyl)oxy]-N-methyl-N-[2-(dimethylamino)cyclohexyl]acetamide;

trans-N-[2-(Dimethylamino)cyclohexyl]-N-methyl-2-[(2-nitro-1-naphthalenyl)oxy]acetamide;

The free base form of compounds of the present invention are converted, if desired, by known methods to the corresponding acid addition salts by reaction with a number of pharmaceutically acceptable organic and inorganic acids. Suitable acids for this purpose include hydrochloric, hydrobromic, hydriodic, sulfuric, nitric, phosphoric, acetic, benzoic, citric, maleic, tartaric, succinic, gluconic, ascorbic, sulphamic, oxalic, pamoic, methanesulfonic, benzenesulfonic and mixtures thereof.

The salts are produced by contacting the free base form of the compounds of this invention with an equivalent amount of the desired acid in a suitable polar solvent such as water, an alcohol, or aqueous alcohol. The solvent is removed to yield the salt which may be used as such or further purified by recrystallization.

The free base form of the compound may be regenerated, if desired, by contacting the salt form with an aqueous solution of a base such as sodium hydroxide, potassium carbonate, sodium bicarbonate, ammonia, and the like.

The free base form of the compounds of this invention differ from their corresponding acid addition salts in such physical characteristics as melting point and solubility in polar solvents, but are otherwise considered equivalent for the purposes of this invention.

The compounds of the present invention and/or their pharmaceutically acceptable acid addition salts possess significant analgesic activity with potential for minimum dependence liability due to their selective kappa opioid receptor binding properties. In addition to analgesic action, selective kappa opioid agonists such as the compounds of the present invention also cause opioid receptor-mediated sedation, diuresis, and corticosteroid elevation. Accordingly, the compounds of the present invention are also useful as diuretics and psychotherapeutic agents as well as analgesics.

Representative examples of compounds of the present invention, when tested in vitro to determine the extent of opioid receptor site binding, were found to selectively bind to the kappa opioid receptors with evidence of much less binding to the delta or mu receptors. The significance of this selective binding has already been mentioned above and is discussed in M. B. Tyers, *Brit. J. Pharmacol.*, 69: 503–512 (1980).

Measurement of the kappa opioid receptor site binding activity of compounds of the present invention was made by the following method. Guinea pig brain homogenates were prepared fresh daily utilizing the method of Gillan et al., *Brit. J. Pharmacol.*, 70: 481–490 (1980).

The binding of tritiated etorphine to brain homogenates was measured in the presence of unlabeled competitor compounds of the present invention with 200 nanomolar D-Ala-D-Leu-enkephalin (acronym DADLE) and 200 nanomolar D-Ala-MePheGly-ol-enkephalin (acronym DAGO). The latter compounds were added to saturate the delta and mu opioid receptors, respectively. The reaction was terminated by rapid filtration and the radioactivity bound to the filters counted by liquid scintillation spectrophotometry.

Measurement of the mu and delta opioid receptor site binding of compounds of the present invention was made by the following method. Guinea pig brain homogenates were prepared fresh daily using the method of Gillan et al., cited above.

Homogenates were incubated for 150 minutes at 0° C. with either tritiated DAGO to measure mu receptor site binding activity, or with tritiated DADLE in the presence of a ten-fold excess of unlabeled DAGO to measure delta opioid receptor site binding activity. Nonspecific binding was determined in the presence of $10^{-6}$ molar DAGO and $10^{-6}$ molar DADLE.

Reactions were terminated by rapid filtration and the radioactivity bound to the filters counted by liquid scintillation spectrophotometry.

The data were analyzed by the methods of Scatchard, *Ann. New York Acad. Sci.*, 51: 660–672 (1949) and Hill, *J. Physiol.*, 40: IV–VIII (1910). The inhibition of binding of tritiated etorphine, DAGO and DADLE was determined from the regression of log percentage of specific binding or log concentration of cold ligand. The inhibition constant, $K_i$, was calculated from the equation:

$$K_i = \frac{IC50}{1 + [L]/KD}$$

where [L] is the molar concentration of labeled ligand where $K_D$, its equilibrium dissociation constant.

Representative examples of compounds of the present invention have shown positive activity in standard laboratory analgesic tests such as the acetylcholine-induced writhing test with mice, and the rat paw pressure test.

In the acetylcholine-induced writhing test, mice which have received a test compound and those which have not are injected intraperitoneally with acetylcholine and the number of characteristics stretching writhes counted. The dose of compound (in mg/kg of body weight) administered subcutaneously and which elicits 50% of the maximum possible effect is recorded as the "$MDE_{50}$" value.

In the rat paw pressure test, mild, but increasing pressure is applied to the paw of both control animals and animals which have been administered sub-cutaneous doses of the test compound. The pressure (in arbitrary units) at which the animal responds to the pressure is recorded. The dose required to elicit 50% of the maximum possible effect is recorded as the "$MDE_{50}$" value. Compounds having an $MDE_{50}$ value of less than 30 mg/kg of body weight are rated "A".

The results of these tests are presented in Table 1.

The compounds of the present invention and/or their non-toxic, pharmaceutically acceptable acid addition salts, may be administered to mammals in pharmaceutical compositions or formulations which comprise one or more of the compounds of this invention and/or salts thereof in combination with a pharmaceutically acceptable non-toxic carrier.

As parenteral compositions, the compounds of this invention may be administered with conventional injectable liquid carriers such as sterile pyrogen-free water, sterile peroxide-free ethyl oleate, dehydrated alcohols, polypropylene glycol, and mixtures thereof.

TABLE 1

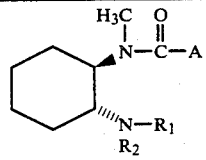

| $R_1 R_2$ | A | Writhing (MDE$_{50}$ mg/kg) | Paw Pressure (Rating) | $K_i$ Kappa | $K_i$ Mu |
|---|---|---|---|---|---|
| Pyrrolidinyl | 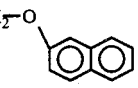 | 1.9 | A | $8 \times 10^{-8}$ | $1 \times 10^{-6}$ |
| Pyrrolidinyl | —CH$_2$—O— (naphthalene) | 1.2 | A | $2.5 \times 10^{-7}$ | $1 \times 10^{-6}$ |

Suitable pharmaceutical adjuvants for the injecting solutions include stabilizing agents, solubilizing agents, buffers, and viscosity regulators. Examples of these adjuvants include ethanol, ethylenediamine tetraacetic acid (EDTA), tartrate buffers, citrate buffers, and high molecular weight polyethylene oxide viscosity regulators. These pharmaceutical formulations may be injected intramuscularly, intraperitoneally,, or intravenously.

As solid or liquid pharmaceutical compositions, the compounds of the present invention may be administered to mammals orally in combination with conventional compatible carriers in solid or liquid form. These oral pharmaceutical compositions may contain conventional ingredients such as binding agents such as syrups, acacia, gelatin, sorbitol, tragacanth polyvinylpyrrolidone, and mixtures thereof.

The compositions may further include fillers such as lactose, mannitols, starch, calcium phosphate, sorbitol, methylcellulose, and mixtures thereof.

These oral compositions may also contain lubricants such as magnesium stearate, high molecular weight polymers such as polyethylene glycol, high molecular weight fatty acids such as stearic acid, silica, or agents to facilitate disintegration of the solid formulation such as starch, and wetting agents such as sodium lauryl sulfate.

The oral pharmaceutical compositions may take any convenient form such as tablets, capsules, lozenges, aqueous or oily suspensions, emulsions, or even dry powders which may be reconstituted with water or other suitable liquid prior to use.

As topically administered pharmaceutical compositions, the compounds of the present invention may be administered in the form of ointments or creams containing from about 0.1% to about 10% by weight of the active component in a pharmaceutical ointment or cream base.

Compounds of the present invention may be rectally administered to mammals in the form of suppositories. For preparing suppositories, a low-melting wax such as a mixture of fatty acid glycerides or cocoa butter is first melted, and the active ingredient is dispersed homogeneously in the melt. The mixture is then poured into convient sized molds and allowed to cool and solidify.

The solid or liquid forms may contain flavorants, sweeteners, and/or preservatives such as alkyl p-hydroxy-benzoates. The liquid forms may further contain suspending agents such as sorbitol, glucose, or other sugar syrups, methyl-, hydroxymethyl-, or carboxymethylcellulose, and gelatin, emulsifying agents such as lecithin or sorbitol monooleate, and conventional thickening agents. The liquid compositions may optionally be encapsulated in, for example, gelatin capsules in an effective amount.

Preferably, the pharmaceutical compositions of this invention are in unit dosage form. In such form, the preparation is subdivided into unit doses containing appropriate amounts of the active component. The unit doses can be a packaged preparation with the package containing discrete quantities of the preparation. For example, the package may take the form of packaged tablets, capsules, and powders in envelopes, vials or ampoules. The unit dosage form can also be a capsule, cachet, or tablet itself or can be the appropriate number of any of these packaged forms.

The quantity of active compound in a unit dose of preparation may be varied or adjusted from about 0.5 mg to about 350 mg according to the particular application and the potency of the active ingredient.

When employed systematically in therapeutic use as analgesic agents in the pharmaceutical method of this invention, the compounds are administered at doses of from about 0.05 mg to about 2.0 mg of active compound per kilogram of body weight of the recipient.

GENERAL SYNTHETIC METHODS

In general, compounds of the present invention are prepared by reacting the appropriate trans-1,2-diaminocyclohexane compound of structural formula 2 above with a carboxylic acid of formula 3 above, or a reactive derivative thereof such as the corresponding acid chloride or acyl imidazole.

The appropriate carboxylic acid 3 may be reacted directly with the cyclic diamine 2 in the presence of a coupling reagent such as dicyclohexylcarbodiimide or the like. The reaction is generally carried out in a suitable solvent such as tetrahydrofuran or dioxane at ambient temperature but, depending upon the the reactivity of the specific starting materials employed, the reaction time, solvent employed, and reaction temperature may be varied. Reaction temperatures between about $-25°$ C. and the boiling point of the solvent are employed.

The reaction between the acid chloride and the cyclic diamine is carried out, generally at ambient temperatures, in a suitable solvent such as chloroform or dichloromethane in the presence of an acid acceptor such as a tertiary amine or an alkali or alkaline earth metal carbonate or bicarbonate. The mixture of amine and acid halide is allowed to stand until the reaction is complete.

Alternatively, the desired starting carboxylic acid may first be converted to the corresponding acyl imidazole compound 4

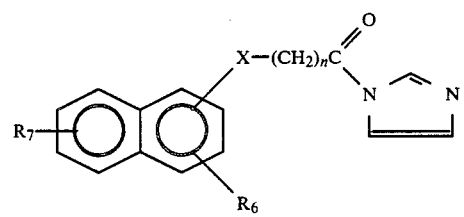

by conventional methods and the acyl imidazole is then reacted with the cyclic diamine compound in the conventional manner.

In an alternative method, the desired carboxylic acid (or reactive derivative thereof) is reacted with trans-N,N'-dimethylcyclohexane to form the intermediate amide where $R_1$ is methyl and $R_2$ is hydrogen. This intermediate is then further reacted with a reactive alkyl, alkenyl, or alkynyl halide such as allyl chloride or bromide, or propargyl chloride or bromide, or the like to form the compounds where $R_2$ is allyl, propargyl, etc.

The desired product from any of the foregoing methods is recovered from the reaction mixture by techniques well known to practitioners of the organic chemical arts. For example, the reaction mixture can be concentrated under vacuum, if desired, to remove the solvent and other volatile components of the reaction mixture to yield the product, usually as an oil. This residual material is then taken up in a solvent such as diethyl ether, washed first with a solution of a salt such as sodium bicarbonate, and then with water. The organic phase is separated, dried over magnesium sulfate, and the organic solvent is evaporated to yield the desired product as an oil or crystalline solid.

The starting trans-1,2-diaminocyclohexane compounds are prepared by the methods detailed in U.S. Pat. No. 4,145,435.

The starting carboxylic acids are known or, if novel, are prepared by reaction sequences well known in the art and, for the most part, analogous to methods employed in the synthesis of the known acid compounds.

Acid chlorides of the starting carboxylic acids are prepared by reaction of the acid compounds with, for example, thionyl chloride.

The acyl imidazole derivatives 4 of the carboxylic acids are prepared by reacting carbonyldiimidazole with the appropriate acid in the conventional manner.

The following preparative examples are provided to enable one skilled in the art to practice the present invention. However, these examples should not be read as limiting the scope of the present invention as defined by the appended claims, but merely as illustrative thereof.

EXAMPLE 1 trans-N-Methyl-2-(1-pyrrolidinyl)cyclohexanamine

The first step in the preparation of the title compound involved the preparation of 7-methyl-7-azabicyclo[4.1.0]heptane by a modification of the method of Taguchi and Eto [see J. Am. Chem. Soc., 80:4076 (1958)]. Cyclohexene oxide (Aldrich Chemical Co., Milwaukee, Wis., USA, 196.3 g, 2 mol) was added dropwise to a 25% solution of aqueous methylamine (745 ml, 6 mol) with stirring and cooling over a period of one hour. During this time, the temperature of the mixture reached 46° C. The resulting mixture was stirred at room temperature overnight, and then heated under reflux for three hours.

The mixture was then cooled in an ice-bath and saturated with solid NaOH, extracted four times with 200-ml portions of ether, dried over anhydrous magensium sulfate, and evaporated to dryness.

The crude product was distilled under water vacuum to yield 208 g (81%) of trans-2-(methylamino)cyclohexanol, bp 118° C. (water vacuum).

The trans-2-(methylamino)cyclohexanol (208 g, 1.61 mol) from the previous step was placed in a three-liter beaker and dissolved in 400 ml of ether. Chlorosulphonic acid (189 g, 1.62 mol) was added dropwise over a period of one hour to the ice-salt cooled mixture. An additional 200 ml of ether were added, and the mixture was stirred.

The mixture was allowed to warm to room temperature and to stand for three hours. The ether supernate was decanted and the residual white solid washed with 300 ml of ether which was also decanted.

The residual solid was cooled in an ice-salt bath and NaOH (218 g dissolved in 1 liter of water) was slowly added. The thick white solid which resulted was allowed to stand overnight at room temperature.

The crude product, 7-methyl-7-azabicyclo[4.1.0]heptane, was distilled with continuous addition of water from an addition funnel in order to maintain constant original volume. After 600 ml of distillate had been collected, the total distillate was saturated with solid NaOH, extracted five times with 200-ml portions of ether, dried over anhydrous magnesium sulfate, and the ether evaporated.

The residue was distilled using a water vacuum and air bleed to yield 67 g (37%) of 7-methyl-7-azabicyclo[4.1.0]heptane, bp 38° C. (water vacuum, air bleed).

7-Methyl-7-azabicyclo[4.1.0]heptane (7.0 g, 0.063 mol) from the previous step, 17.92 g (0.25 mol) of pyrrolidine, 0.16 g of ammonium chloride, and 10 ml of water were stirred and heated under reflux for 21 hours. The solution was then cooled and solid sodium hydroxide was added and the mixture was extracted three times with 50-ml portions of ether. The combined extracts were dried over anhydrous magnesium sulfate and evaporated under reduced pressure to yield a residual brown oil. This residue was distilled under high vacuum to yield 6.0 g of colorless trans-N-methyl-2-(1-pyrrolidinyl)cyclohexanamine, bp 95° C. (high vacuuum).

EXAMPLE 2 trans-N,N'-Dimethylcyclohexane-1,2-diamine

7-Methyl-7-azabicyclo[4.1.0]heptane (36.1 g prepared by the method detailed in Example 1), methylamine (162 ml of a 23–30% aqueous solution) and 0.5 g of ammonium chloride were heated in an oil bath at 94°14 99° C. for 21.5 hours. After cooling to 0° C. the mixture was treated with 10 g of solid sodium hydroxide and extracted four times with 100 ml portions of ether. The combined ether extracts were dried over anhydrous magnesium sulfate, the ether evaporated, and the residue distilled to yield 18 g (39%) of trans-N,N'-dimethylcyclohexane-1,2-diamine, bp 78° C. (at a pressure of 1866 Pascal) which solidified upon standing to a solid which melted at 17° C.

Analysis—found: C, 67.5%; H, 13.1%; N, 19.65%. Calc. for $C_8H_{18}N_2$: C, 67.55%; H, 12.75%; N, 19.7%.

EXAMPLE 3 trans-N-Methyl-2-(1-piperidinyl)cyclohexanamine

A stirred mixture of 7-methyl-7-azabicyclo[4.1.0]heptane (5.0 ml, 39 mmol), piperidine (3.9 ml, 39 mmol) and 0.2 g of ammonium chloride dissolved in 0.4 ml of water was heated under reflux for 5.5 hours. Normal work-up of the reaction mixture followed by bulb-to-bulb distillation yielded 3.2 g (42%) of trans-N-methyl-2-(1-piperidinyl)cyclohexanamine as a colorless liquid, bp 210° C. (at a pressure of 2666 Pascal).

EXAMPLE 4 trans-2-(Dimethylamino)-N-methylcyclohexanamine

Employing the general method of Examples 1, 2, or 3, the title compound was prepared by reacting 7-methyl-7-azabicyclo[4.1.0]heptane with dimethylamine in a pressure vessel at 1378 kPascal and 85° C. The product was an oil, b.p. 90–100 (at a pressure of 300 Pascal).

EXAMPLE 5 trans-N-Methyl-2-(2-naphthalenyloxy)-N-[2-(1-pyrrolidinyl)cyclohexyl]acetamide, hydrochloride 2-Naphthalenyloxyacetic acid (404 mg, 2 mmol,) and 5 ml of thionyl chloride were stirred at room temperature for 16 hours and then heated to reflux. The mixture was cooled and the excess thionyl chloride was removed under reduced pressure by azeotropic distillation with carbon tetrachloride.

The resulting 2-naphthalenyloxyacetyl chloride was dissolved in 20 ml of methylene chloride, and 364 mg (2 mmol) of trans-N-methyl-2-(1-pyrrolidinyl)cyclohexylamine (prepared as described above in Example 1) in 5 ml of methylene chloride were added with stirring.

After the reaction was complete, the solution was filtered and evaporated to a small volume. Diethyl ether was added until no more precipitate formed. The crystalline product was collected by filtration, washed with diethyl ether, and dried in a vacuum oven at 80° C. overnight to yield 431 mg (54%) of trans-N-methyl-2-

(2-naphthalenyloxy)-N-[2-(1-pyrrolidinyl)cyclohexyl]acetamide, hydrochloride, m.p. 232°-236° C. (infrared absorption maximum, 1655 cm$^{-1}$ in a Nujol mineral oil mull).

EXAMPLE 6 trans-N-Methyl-2-(1-naphthalenyloxy)-N-[2-(1-pyrrolidinyl)cyclohexyl]acetamide, hydrochloride 1-Naphthylenyloxyacetic acid (404 mg, 2 mmol, Shibata et al., *Tech Repts. Tohoku Imp. Univ.*, 12:119-135 (1936)), and 5 ml of thionyl chloride were heated under reflux until no solid remained. The mixture was cooled to room temperature and the excess thionyl chloride was removed under reduced pressure. The residual thionyl chloride was removed by azeotropic distillation with carbon tetrachloride.

The resulting 1-naphthalenyloxyacetyl chloride was dissolved in 20 ml of 1:1 methylene chloride:diethyl ether, and 364 mg (2 mmol) of trans-N-methyl-2-(1-pyrrolidinyl)cyclohexylamine (prepared as described above in Example 1) in 3 ml of methylene chloride were added with stirring.

The mixture was stirred for 30 minutes then cooled to 0° C. and diethyl ether was added until no more precipitate formed. After stirring for an additional 15 minutes, the crystalline product was collected by filtration and washed with diethyl ether. The product was dried overnight at 80° C. in a vacuum oven to yield 737 mg (92%) of trans-N-methyl-2-(1-naphthalenyloxy)-N-[2-(1-pyrrolidinyl)cyclohexyl]acetamide, hydrochloride, m.p. 153°-58° C. and again at 205°-215° C. (infrared absorption maximum, 1660 cm$^{-1}$ in a Nujol mineral oil mull).

EXAMPLE 7 trans-2-[(4-Chloro-1-naphthalenyl)oxy]-N-methyl-N-[2-(1-pyrrolidinyl)cyclohexyl]acetamide, hydrochloride Starting with trans-N-methyl-2-(1-pyrrolidinyl)cyclohexanamine and 4-chloro-1-(naphthalenyloxy)acetic acid, the title compound, m.p. 201°-204° C., was prepared employing the method of Example 5.

EXAMPLE 8 trans-2-[(4-Methoxy-1-naphthalenyl)oxy]-N-methyl-N-[2-(1-pyrrolidinyl)cyclohexyl]acetamide, hydrochloride Starting with trans-N-methyl-2-(1-pyrrolidinyl)cyclohexanamine and [(4-methoxy-1-naphthalenyl)oxy]acetic acid, the title compound, m.p. 207°-211° C. was prepared employing the method of Example 5.

EXAMPLE 9 trans-N-Methyl-2-[(2-methyl-1-naphthalenyl)oxy]-N-[2-(1-pyrrolidinyl)cyclohexyl]acetamide, methanesulphonate Starting with trans-N-methyl-2-(1-pyrrolidinyl)cyclohexanamine and 2-methyl-1-naphthalenyloxyacetic acid, the title compound, m.p. 204°-206° C., was prepared employing the method of Example 5. The methanesulphonate salt was prepared by shaking a solution of the initially prepared crude hydrochloride salt in methylene chloride with excess aqueous sodium bicarbonate solution to produce the free base, and then adding one equivalent of methanesulphonic acid to the free base and allowing the salt to crystallize.

EXAMPLE 10 trans-2-[(4-Chloro-1-naphthalenyl)oxy]-N-[2-(dimethylamino)cyclohexyl]-N-methylacetamide, hydrochloride Starting with trans-2-dimethylamino-N-methylcyclohexanamine and [(4-chloro-1-naphthalenyl)oxy]acetic acid, the title compound, m.p. 135°-138° C., was prepared employing the method of Example 5.

EXAMPLE 11 trans-N-[2-(dimethylamino)cyclohexyl]-2-[(4-methoxy-1-naphthalenyl)oxy]-N-methylacetamide, hydrochloride Starting with trans-2-dimethylamino-N-methylcyclohexanamine and [(4-methoxy-1-naphthalenyl)oxy]acetic acid, the title compound, m.p. 226°-230° C., was prepared employing the method of Example 5.

EXAMPLE 12 trans-N-[2-(Dimethylamino)cyclohexyl]-N-methyl-2-[(2-methyl-1-naphthalenyl)oxy]acetamide, methanesulphonate Starting with trans-2-(dimethylamino)-N-methylcyclohexanamine and [(2-methyl-1-naphthalenyl)oxy]acetic acid, the title compound, m.p. 144°-147° C., was prepared employing the method of Example 5. The methanesulphonate salt was prepared from the initially prepared hydrochloride salt by the method detailed in Example 9.

We claim:

1. A compound having structural formula 1

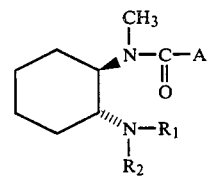

wherein

R$_1$ and R$_2$ taken together with the nitrogen atom to which they are attached form a pyrrolidinyl ring; and where A is

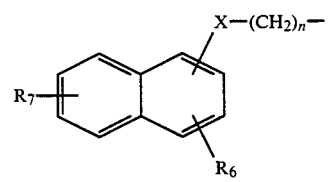

where n is an integer of from one to six; X is oxygen or sulfur; and R$_6$ and R$_7$ are independently hydrogen, fluorine, chlorine, bromine, nitro, alkyl of from one to four carbon atoms, alkoxy of from one to four carbon atoms, or acetoxy; or an N-oxide of the pyrrolidinyl nitrogen atom or pharmaceutically acceptable acid addition salts thereof.

2. A compound as defined by claim 1 wherein X is oxygen.

3. A compound as defined by claim 2 wherein A is

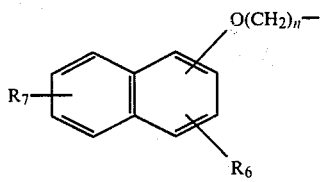

where n is an integer of from one to six; and R₆ and R₇ are independently hydrogen, fluorine, chlorine, nitro, alkyl of from one to four carbon atoms, alkoxy of from one to four carbon atoms or acetoxy; and the pharmaceutically acceptable acid addition salts thereof.

4. A compound as defined by claim 3 having the name N-methyl-2-(1-naphthalenyloxy)-N-[2-(1-pyrrolidinyl)-cyclohexyl]acetamide and the pharmaceutically acceptable acid addition salts thereof.

5. A compound as defined by claim 3 having the name N-methyl-2-(2-naphthalenyloxy)-N-[2-(1-pyrrolidinyl)-cyclohexyl]acetamide and the pharmaceutically acceptable acid addition salts thereof.

6. A compound as defined by claim 3 having the name trans-N-methyl-2-[(2-methyl-1-naphthalenyl)oxy]-N-[2-(1-pyrrolidinyl)cyclohexyl]acetamide and the pharmaceutically acceptable acid addition salts thereof.

7. A compound as defined by claim 3 having the name trans-2-[(2-chloro-1-naphthalenyl)oxy]-N-methyl-N-[2-(1-pyrrolidinyl)cyclohexyl]acetamide and the pharmaceutically acceptable acid addition salts thereof.

8. A compound as defined by claim 3 having the name trans-2-[(4-chloro-1-naphthalenyl)oxy]-N-methyl-N-[2-(1-pyrrolidinyl)cyclohexyl]acetamide and the pharmaceutically acceptable acid addition salts thereof.

9. A compound as defined by claim 3 having the name trans-2-[(2,4-dichloro-1-naphthalenyl)oxy]-N-[2-(1-pyrrolidinyl)cyclohexyl]-N-methylacetamide and the pharmaceutically acceptable acid addition salts thereof.

10. A compound as defined by claim 3 having the name trans-2-[(2-acetoxy-1-naphthalenyl)oxy]-N-methyl-N-[2-(1-pyrrolidinyl)cyclohexyl]acetamide and the pharmaceutically acceptable acid addition salts thereof.

11. A compound as defined by claim 3 having the name trans-2-[(4-methoxy-1-naphthalenyl)oxy]-N-methyl-N-[2-(1-pyrrolidinyl)cyclohexyl]acetamide and the pharmaceutically acceptable acid addition salts thereof.

12. A compound as defined by claim 3 having the name trans-N-methyl-2-[(2-nitro-1-naphthalenyl)oxy]-N-[2-(1-pyrrolidinyl)cyclohexyl]acetamide and the pharmaceutically acceptable acid addition salts thereof.

13. A pharmaceutical composition useful for treating pain in a mammal comprising an analgesically effective amount of a compound in accordance with claim 1 in combination with a pharmaceutically acceptable carrier.

14. A method of treating pain in a mammal comprising administering to a mammal in need of such treatment an analgesically effective amount of a compound in accordance with claim 1 in combination with a pharmaceutically acceptable carrier.

* * * * *